(12) United States Patent
Olbert et al.

(10) Patent No.: US 7,402,288 B2
(45) Date of Patent: Jul. 22, 2008

(54) REACTOR FOR TESTING CATALYST SYSTEMS

(75) Inventors: Gerhard Olbert, Dossenheim (DE); Torsten Mattke, Freinsheim (DE); Matthias Kummer, Weisenheim (DE); Thomas Ruehl, Frankenthal (DE); Frank Rosowski, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 970 days.

(21) Appl. No.: 10/478,684

(22) PCT Filed: Jun. 5, 2002

(86) PCT No.: PCT/EP02/06177

§ 371 (c)(1), (2), (4) Date: Dec. 5, 2003

(87) PCT Pub. No.: WO02/098551

PCT Pub. Date: Dec. 12, 2002

(65) Prior Publication Data

US 2004/0126285 A1 Jul. 1, 2004

(30) Foreign Application Priority Data

Jun. 6, 2001 (DE) .................. 101 27 374

(51) Int. Cl.
*B01J 19/24* (2006.01)
*F27B 15/14* (2006.01)
*F28D 7/16* (2006.01)
*G01N 31/10* (2006.01)

(52) U.S. Cl. .................. 422/138; 422/129; 422/130; 422/131; 422/146; 422/198; 422/200; 422/201; 436/37

(58) Field of Classification Search .................. 422/129, 422/130–131, 138, 146, 198, 200–201; 436/37
See application file for complete search history.

(56) References Cited

U.S. PATENT DOCUMENTS 3,792,980 A * 2/1974 Vollmer et al. .............. 422/205

(Continued)

FOREIGN PATENT DOCUMENTS

DE 27 14 939 10/1978

(Continued)

OTHER PUBLICATIONS

Landon, V. G. Computers & Chemical Engineering 1996, 20, 475-481.*

*Primary Examiner*—Arlen Soderquist
(74) *Attorney, Agent, or Firm*—Oblon, Spivak, McClelland, Maier & Neustadt, P.C.

(57) ABSTRACT

A reactor for testing catalyst systems which has a plurality of catalyst tubes (2) which are arranged parallel to one another in the interior space of the reactor and whose ends are welded into tube plates and also has caps (3) at each end of the reactor which each bound a cap space (4), with a fluid reaction medium (5) being fed via one cap space (4) into the catalyst tubes (2), flowing through the catalyst tubes (2) and being discharged via the other cap space (4), and is also provided with a heat exchange medium circuit in which the heat exchange medium (6) is fed in at one end of the reactor, flows through the intermediate space between the catalyst tubes (2) and flows out at the other end of the reactor, wherein the catalyst tubes (2) are arranged in two or more catalyst tube regions (7) which are thermally separate from one another, is proposed.

9 Claims, 7 Drawing Sheets

U.S. PATENT DOCUMENTS

| | | | |
|---|---|---|---|
| 4,203,906 A * | 5/1980 | Takada et al. | 549/248 |
| 4,207,264 A * | 6/1980 | Anderson et al. | 568/385 |
| 4,597,946 A * | 7/1986 | Ward | 422/190 |
| 4,873,368 A * | 10/1989 | Kadowaki et al. | 562/532 |
| 6,333,011 B1 * | 12/2001 | Schliephake et al. | 422/197 |
| 6,419,884 B1 | 7/2002 | Strobel et al. | |

FOREIGN PATENT DOCUMENTS

| | | | |
|---|---|---|---|
| DE | 28 30 765 | | 1/1980 |
| EP | 0 911 313 | | 4/1999 |
| WO | 00/17946 | * | 3/2000 |

* cited by examiner

REACTOR FOR TESTING CATALYST SYSTEMS

The present invention relates to a reactor for testing catalyst systems, to a test method and to a use.

In the chemical industry, many large-scale reactions, are carried out in shell-and-tube reactors containing catalysts. In such reactions, a fluid, frequently gaseous, reaction medium is passed through many, frequently from 10 000 to 40 000, tubes which are filled with a catalyst system, i.e. a catalyst support onto which an active material has been applied or an unsupported bulk catalyst. A heat exchange medium, for example a salt melt, flows through the intermediate space between the catalyst tubes to supply or remove heat.

To test new catalyst systems or known catalyst systems in conjunction with new reaction media, use has hitherto been made of pilot-scale reactors provided with a plurality of tubes which were each filled with the same catalyst system to be tested and around which a heat exchange medium flowed. Such a reactor was therefore not available for further uses while a catalyst system was being tested.

It is an object of the present invention to provide a reactor and a test method by means of which a plurality of catalyst systems can be tested simultaneously or one catalyst system can be tested simultaneously under different conditions.

The achievement of this object starts out from a reactor for testing catalyst systems which has a plurality of catalyst tubes which are arranged parallel to one another in the interior space of the reactor and whose ends are welded into tube plates and also has caps at each end of the reactor which each bound a cap space, with a fluid reaction medium being fed via one cap space into the catalyst tubes, flowing through the catalyst tubes and being discharged via the other cap space, and is also provided with a heat exchange medium circuit in which the heat exchange medium is fed in at one end of the reactor, flows through the intermediate space between the catalyst tubes and flows out at the other end of the reactor. In the reactor of the present invention, the catalyst tubes are arranged in two or more catalyst tube regions which are thermally separate from one another.

The reactor of the present invention is generally a pilot-scale reactor, but the invention is not restricted in terms of the reactor size. The reactor shape is frequently, but not necessarily, cylindrical. For example, a rectangular or polygonal reactor cross section is also possible. In the interior space of the reactor, a plurality of catalyst tubes, at least 10, preferably at least 20, are arranged parallel to one another in the direction of the longitudinal axis of the reactor and are welded into tube plates at their ends. The indicated minimum number of catalyst tubes is necessary to obtain representative measurements for catalytic shell-and-tube reactors. At each end of the reactor there is a cap which in each case bounds a cap space. A fluid, frequently gaseous reaction medium is fed into the reactor via a cap space, flows through the catalyst tubes and is discharged via the other cap space. A heat exchange medium flows through the intermediate space between the catalyst tubes, being fed in at one end of the reactor and discharged at the other end of the reactor.

According to the present invention, the catalyst tubes are arranged in two or more, preferably in four, catalyst tube regions which are thermally separate from one another. For the present purposes, thermally separate does not mean total insulation of the individual catalyst tube regions from one another, but it is necessary for the catalyst tube regions to be sufficiently separated from one another for no substantial heat exchange to take place between the individual catalyst tube regions.

For this purpose, it is generally sufficient for at least one dummy tube or solid round rod having the same external diameter as the catalyst tubes to be arranged in each case between two adjacent catalyst tubes belonging to different catalyst tube regions. The dummy tubes are tubes which are closed at both ends so that reaction medium cannot flow through them. The solid rods are frequently iron rods. It is necessary for the external diameter to be the same as that of the catalyst tubes to ensure identical conditions of flow around them. The installation of the dummy tubes or solid round rods between the catalyst tube regions should be such that no bypasses for the heat exchange medium are created. The arrangement of the catalyst tubes over the total cross section of the reactor is preferably not altered by the formation of catalyst tube regions by means of dummy tubes or solid rods compared to a known reactor without catalyst tube regions, so that disturbance of the flow behavior of the heat exchange medium through the intermediate space between the catalyst tubes is avoided.

It is advantageous to provide at least one catalyst tube in each of one or more catalyst tube regions with a sheath for accommodating a thermocouple and otherwise to fill it with inert material, in particular a bed of aluminum oxide, and to close it at both ends. This arrangement enables the temperature profile of the heat exchange medium flowing around the catalyst tubes in the longitudinal direction of the reactor to be determined. Filling the tube with inert material is advantageous in order to be able to determine the temperature of the heat exchange medium flowing around the catalyst tubes accurately by means of the thermocouple. A suitable inert material is, in particular, a bed of aluminum oxide whose particle size and shape is advantageously selected so that it is readily pourable. Mean particle sizes of from 1 to 5 mm, preferably about 2 mm, are particularly useful. The catalyst tube has to be closed, advantageously at both ends thereof, to prevent reaction mixture from flowing through it.

One or more catalyst tubes in each of one or more catalyst tube regions can advantageously be provided with sheaths for accommodating sampling tubes and/or thermocouples. The configuration of the sheaths and the sampling tubes and/or thermocouples located therein is preferably as described in the German patent application DE 101 10 847.8, which is not a prior publication and is hereby fully incorporated by reference into the disclosure of the present invention.

It is advantageous to choose a greater external diameter, in particular an about 2-3 mm greater external diameter, for the catalyst tubes which are provided with sheaths for accommodating sampling tubes and/or thermocouples compared to the remaining catalyst tubes in order to compensate the volume occupied in the interior of the tube by the sheath and thus avoid falsification of the actual concentration or temperature profile in the catalyst tube.

Similarly, it is also possible for the catalyst tubes which are provided with a sheath for accommodating a thermocouple and are otherwise filled with inert material and closed at both ends and serve for measuring the longitudinal temperature profile of the heat exchange medium to be given a correspondingly greater external diameter.

In a preferred alternative, the catalyst tubes in different catalyst tube regions can have different internal tube diameters and/or different tube spacing. The term tube spacing here refers in a known manner to the distance between the center points of two adjacent catalyst tubes. Preference is given to the triangular spacing, i.e. arrangement of the center points of adjacent catalyst tubes at the corners of an equilateral triangle.

It can be advantageous to provide a cover for the catalyst tubes of one or more catalyst tube regions. This makes it possible to allow the reaction medium to flow in via the cap space, flow through the catalyst tube region or regions which are not covered and subsequently leave the reactor via the other cap space. In such a case, the reaction medium does not flow through the catalyst system in the catalyst tube region(s) which are covered. This makes it possible, for example, to operate the catalyst tube regions which are not covered under more severe conditions without the catalyst system in the covered catalyst tube region(s) being influenced or damaged.

In a further embodiment, it is possible for the cap space via which the reaction medium is taken off to be divided by means of dividing walls so that the reaction medium can be taken off separately from each catalyst tube region. This embodiment has, in particular, the advantage that it is necessary to provide only one analytical facility which can be switched as required to the individual catalyst tube regions. Alternatively or in addition, the other cap space which serves for introduction of the reaction medium can be divided in the same way. These reactor variants further increase the flexibility in terms of the way in which the reaction medium is passed through the reactor. For example, it is in this way possible, particularly in the variant with division of both cap spaces, for the reaction medium which is taken off from one catalyst tube region to be fed, optionally with the intermediate introduction of further starting materials and/or intermediate cooling via an external heat exchanger, into a further catalyst tube region. This procedure can likewise be extended to further catalyst tube regions, in particular to all catalyst tube regions, with in each case the reaction medium being taken off from one catalyst tube region and, optionally after intermediate introduction of further starting materials and/or intermediate cooling, into a subsequent catalyst tube region. This makes it possible, in particular, for a reactor to be used to simulate a larger reactor whose catalyst tubes are two or more times as long.

Further flexibility is achieved by means of a preferred reactor variant in which the intermediate space through which heat exchange medium flows between the catalyst tubes is divided by means of dividing walls into two or more, preferably four, chambers which each correspond to one contact tube region. In this way, a separate circuit for heat exchange medium can be achieved for each individual catalyst tube region. The individual heat exchange medium circuits can be operated independently of one another, in particular in respect of cocurrent or countercurrent passage of the reaction medium, in respect of coolant temperature and/or volume flow of the heat exchange medium. The individual chambers for the heat exchange medium are sealed against the interior wall of the reactor, in particular by means of metal seals. Thereby all kind of sealing elements known in the art can be used for example springy sealing elements with guided metallic sealing strips.

In a particular variant, one or more heat exchange medium circuits are each provided with a specially designed pump which makes it possible for the heat exchange medium, in particular a salt melt, to be conveyed in a downward direction, as is the case for a customary pump arrangement, but with the heat exchange medium nevertheless entering the intermediate space between the catalyst tubes in the upper region of this intermediate space. In this way, cocurrent passage of fluids can be achieved in a simple manner with the customary passage of the reaction medium from the top downward.

This variant comprises a reactor with a vertical longitudinal axis, with introduction of the heat exchange medium into the intermediate space between the catalyst tubes in the upper region of the reactor and discharge of the heat exchange medium from the lower region of the reactor, preferably via a a ring line in each case, with the heat exchange medium taken off from the lower region of the reactor by means of a pump flowing into a housing which encloses the pump guide tube, flowing upward in the region between the interior wall of the housing and the outer wall of the pump guide tube, optionally via a heat exchanger, flowing into the interior space of the pump guide tube via an opening in the upper region of the pump guide tube, flowing from the top downward through this space, flowing into a further region between the interior wall of the housing and the outer wall of the pump guide tube via an opening in the lower region of the pump guide tube, flowing from the bottom upward through this region and flowing into the upper region of the intermediate space between the catalyst tubes via an opening in the upper region of this space.

The housing can advantageously be manufactured with a rectangular cross section, but it is also possible to provide the housing with a circular cross section, particularly for relatively high operating pressures.

The invention also provides a method of testing catalyst systems by means of a reactor, where catalyst systems which differ in respect of the active material and/or the catalyst support, in particular the material and/or the shape and/or the size of the particles of the catalyst support, are tested in different catalyst tube regions. Here, different catalyst systems can be tested simultaneously under identical or different conditions or a given catalyst system can be tested under various conditions at the same time.

The studies allow conclusions to be made as to the suitability of the catalyst system under prescribed, intended operating conditions. It is possible to optimize the future operation of a production reactor and to test the long-term behavior of catalyst systems, in particular over long periods of time.

A particularly preferred variant of the method is cocurrent flow of heat exchange medium and reaction medium, preferably with deflection of the flow of the heat exchange medium in the pump.

Particular preference is given to a method of testing catalyst systems using a reactor in which the parameters of the heat exchange medium in the individual chambers, in particular the flow direction of the heat exchange medium relative to the reaction medium, the temperature and/or the volume flow of the heat exchange medium, can each be set separately. Further preference is given to the reaction medium after it has been taken off from a catalyst tube region via the corresponding region of a cap space being fed, optionally with intermediate introduction of starting materials and/or intermediate cooling, directly into a further catalyst tube region via the corresponding part of a cap space, i.e. without the reaction medium having to be discharged to outside the reactor and fed back into a further catalyst tube region.

The test method of the present invention and the apparatus of the present invention are particularly suitable for testing catalyst systems for exothermic or endothermic reactions, in particular oxidation reactions.

The invention thus provides an extremely flexible reactor for testing catalyst systems which can be described as multifunctional since it makes it possible to run a number of experiments simultaneously. This considerably reduces the time and money required for the experiments. The reactor makes it possible to test the long-term behavior of catalysts even over long periods of time, for example of the order of one year. New catalysts can be used more quickly under production conditions and thus can be evaluated economically more quickly. Furthermore, analytical facilities can be utilized more effectively.

The invention is illustrated below with the aid of a drawing. In the drawing.

Figure 1:
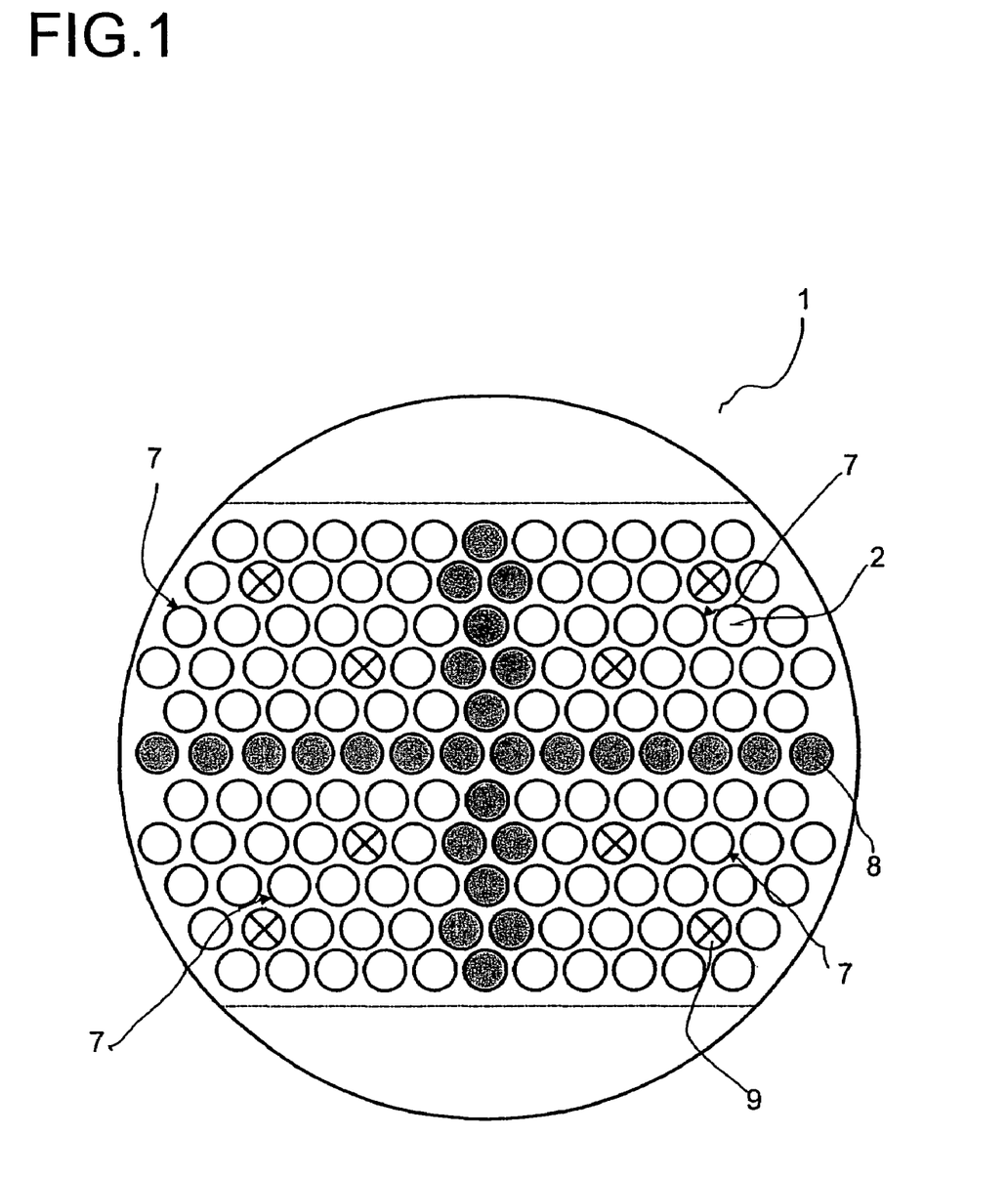
FIG. 1 shows a cross section through a reactor according to the present invention with longitudinal section in FIG. 1a FIG. 2 shows a cross section through a particular embodiment of a cap space.

FIG. 1 shows a cross section through an embodiment of a reactor 1 according to the present invention with catalyst tubes 2 which are divided by way of example into four catalyst tube regions 7 by means of dummy tubes 8 which are filled with inert material. A few catalyst tubes 9 located at a distance from one another are provided with sheaths for sampling tubes and/or thermocouples.

Figure 1A:
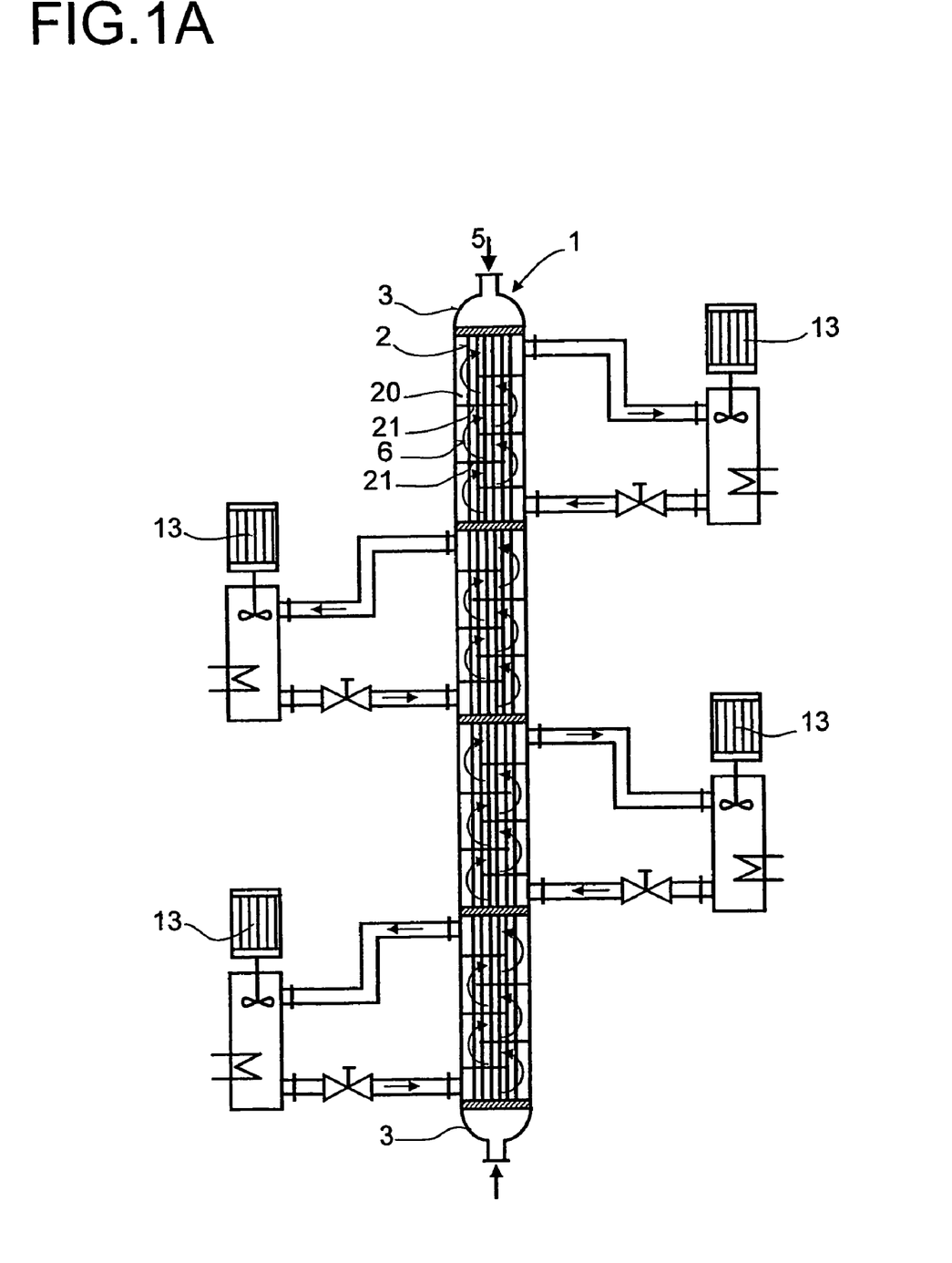

FIG. 1a shows a longitudinal section through the particular embodiment shown in FIG. 1, with four separate heat exchange medium circuits arranged above one another being shown by way of example. Catalyst tubes 2 are arranged in the reactor 1 with caps 3. The reaction medium 5 is passed from the top downward through the reactor and the heat exchange medium 6 is conveyed around four separate circuits located above one another between the catalyst tubes, in each case by means of a pump 13 with deflection of flow by means of deflection plates 21. The reactor 1 is provided with spaces 20 which are free of catalyst tubes for deflecting the heat exchange medium 6.

Figure 2:
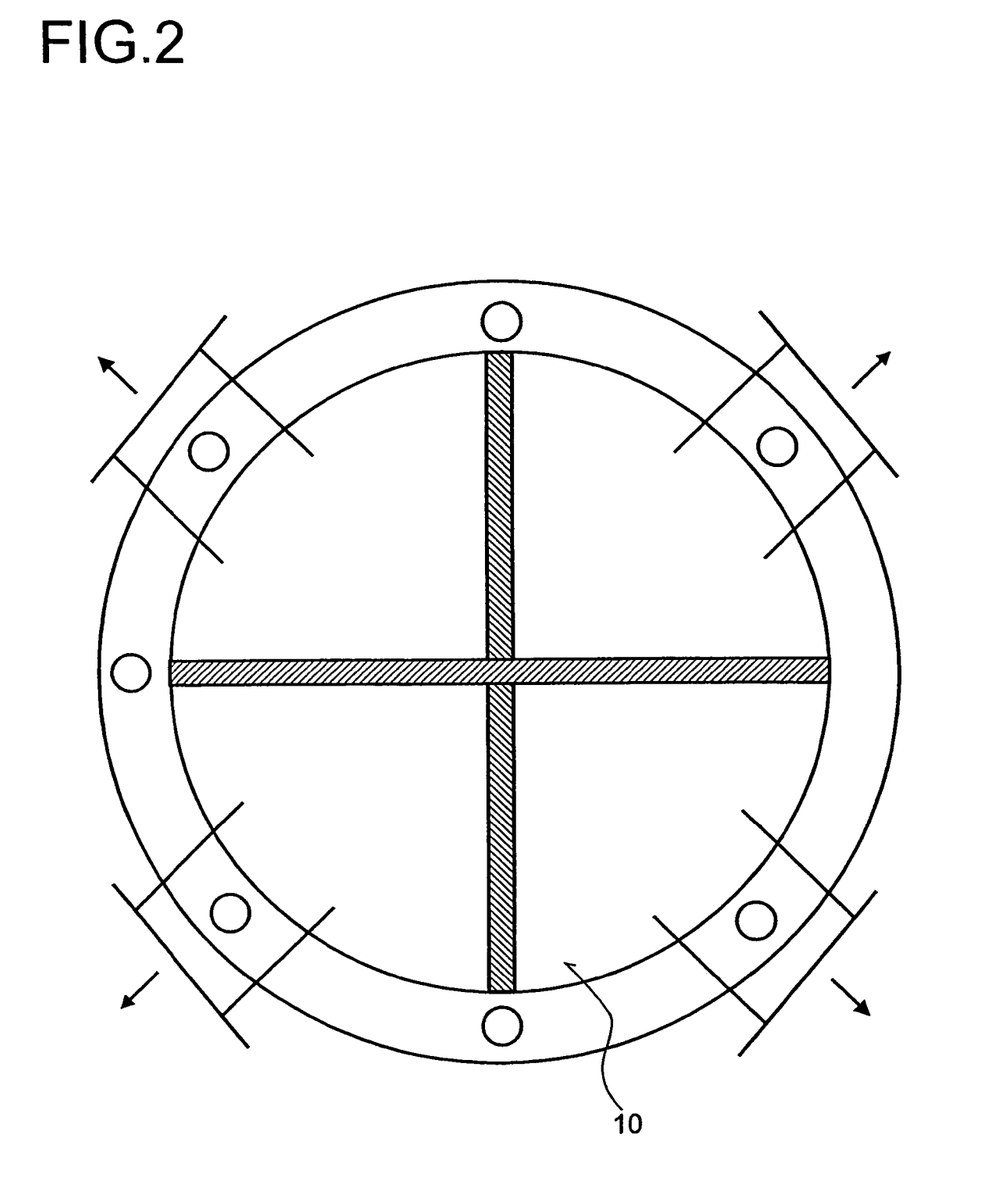

FIG. 2 shows a cross section through a cap space of a particular variant of a reactor 1 according to the present invention, with dividing walls 10 in the cap space dividing this space into four regions assigned to the corresponding catalyst tube regions. The dividing walls 10 can be provided either in the upper or lower cap space or in both cap spaces.

Figure 3:
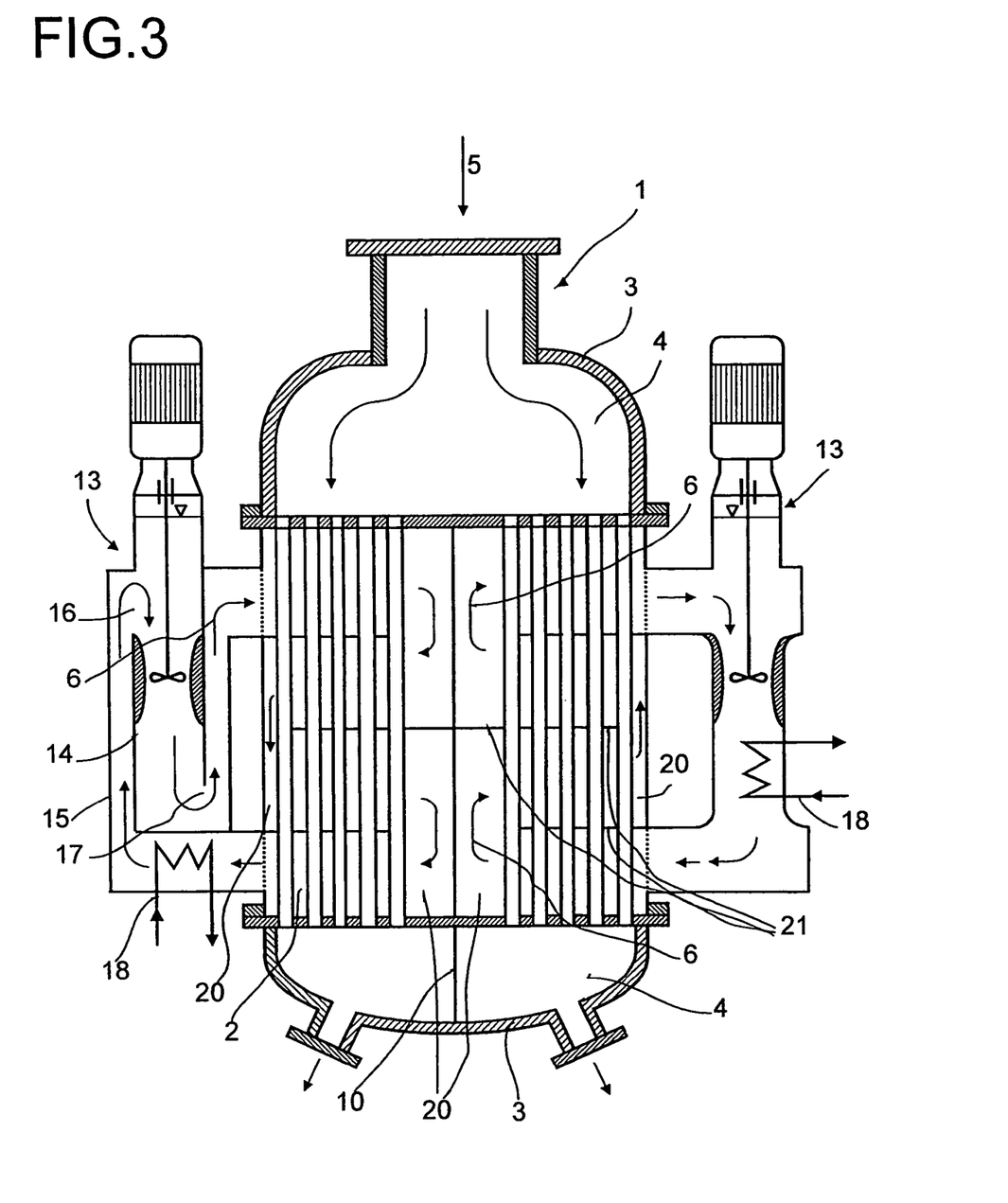
FIG. 3 shows a longitudinal section through a preferred variant with deflection of the heat exchange medium flow in a pump and with four separate cap spaces for taking off the reaction medium.

FIG. 3 shows a longitudinal section through an illustrative embodiment of a reactor 1 according to the present invention with catalyst tubes 2, with spaces 20 which are free of catalyst tubes in the reactor 1 for deflecting the heat exchange medium 6, caps 3, cap spaces 4 and separate heat exchange medium circuits 6, with the right-hand side of the cross section showing countercurrent flow of reaction medium 5 and heat exchange medium 6 and the left-hand half showing cocurrent flow, in each case with deflection of the heat exchange medium 6 in a pump 13. The reaction medium 5 can, as shown by way of example, be fed into the reactor 1 from the top, but it is also equally possible for it to be fed in from below. The reference numeral 14 denotes the pump guide tube with inflow 16 in its upper region and outflow 17 in its lower region and the reference numerals 18 denote heat exchangers which can be located either in the pump itself (as shown on the right-hand side of the longitudinal section) or in the pipe leading to the pump, as shown on the left-hand side in FIG. 3.

Figure 4:
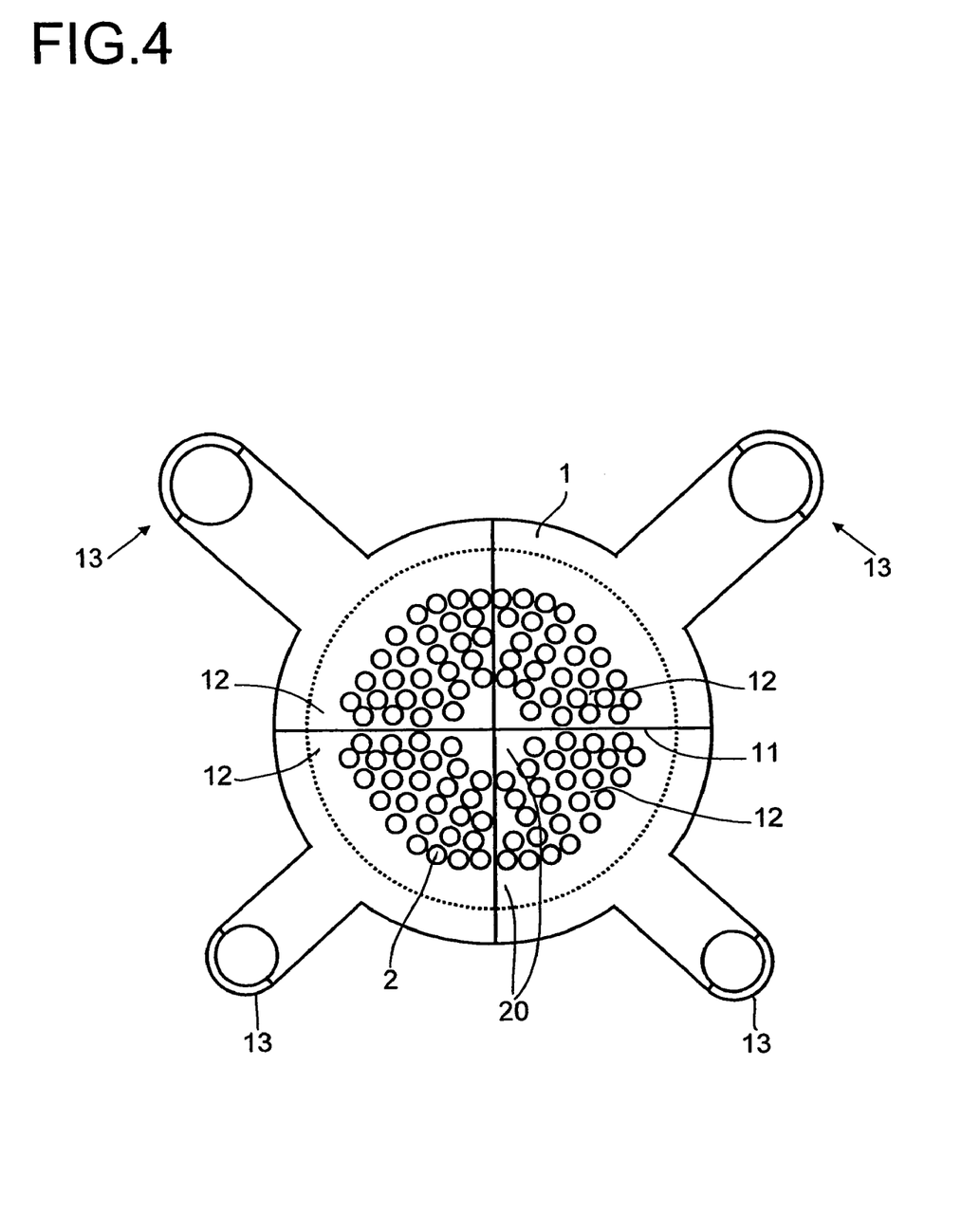
FIG. 4 shows a cross section of the preferred embodiment shown in longitudinal section in FIG. 3.

FIG. 4 shows a cross section through the particular embodiment of a reactor 1 with catalyst tubes 2 according to the present invention shown in longitudinal section in FIG. 3, with dividing walls 11 dividing the intermediate space through which heat exchange medium 6 flows between the catalyst tubes 2 into chambers 12, in the present case four by way of example. The four separate heat exchange medium circuits as shown by way of example in the present case are each maintained by means of a pump 13, with the pumps being drawn larger in the upper part of the diagram compared to the pumps in the lower part of the diagram to indicate that these are pumps with deflection of the heat exchange medium flow 6 in the pump, as illustrated in FIG. 3 in the left-hand part of the cross section.

Figure 5:
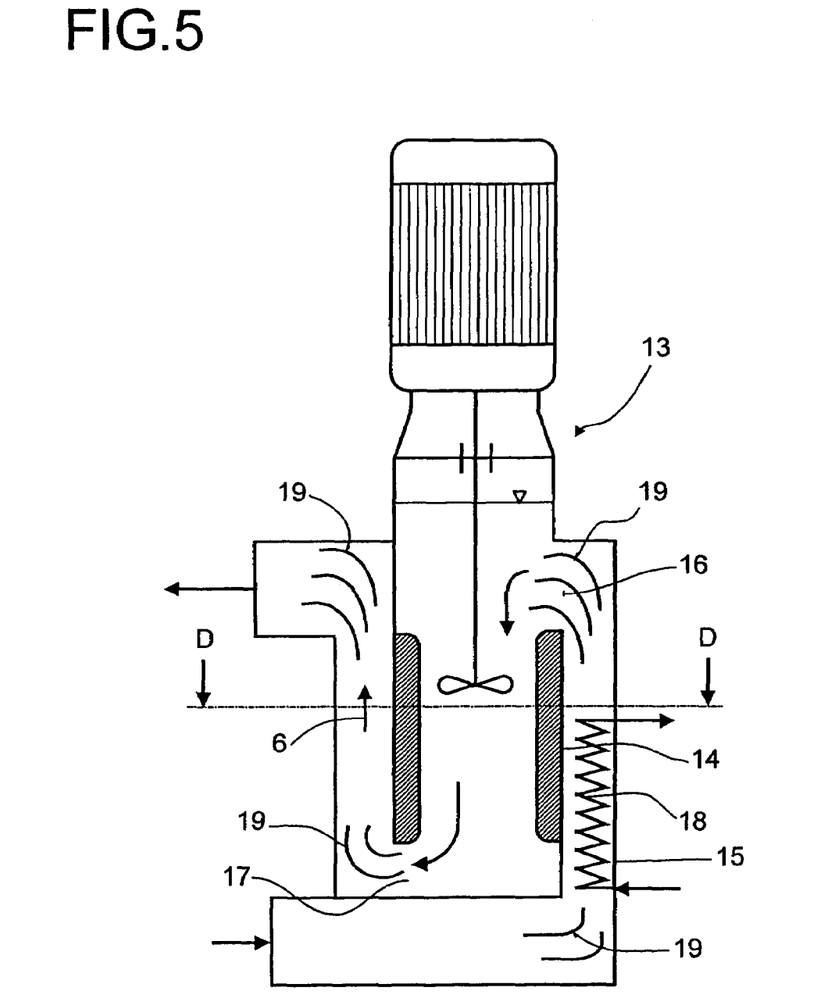
FIG. 5 shows a preferred variant of a pump for deflecting the flow of the heat exchange medium in the pump and FIG. 6 shows a further preferred variant for deflecting the flow of the heat exchange medium in the pump.
Figure 5A:
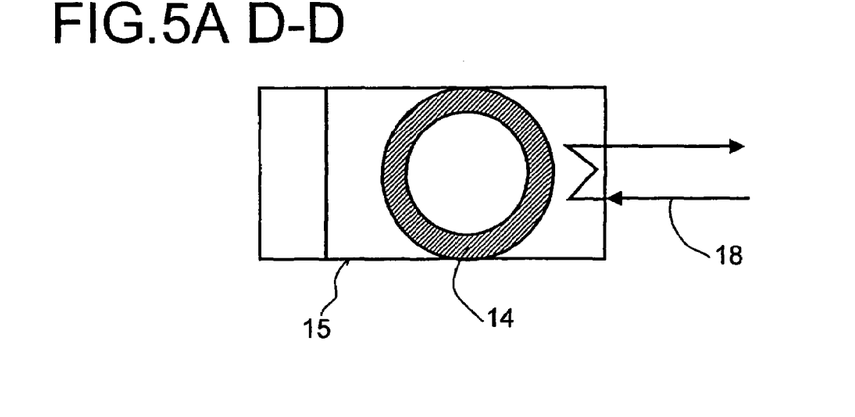

FIG. 5 shows a pump 13 with deflection of the heat exchange medium 6 in the pump, with guide tube 14 with inflow 16 in the upper region and outflow 17 in the lower region of the tube, with housing 15 around the guide tube 14 and a heat exchanger 18 located in the housing 15. The cross section D-D in FIG. 5a clearly shows in cross section the rectangular construction of the housing 15. Deflection plates 19 for the heat exchange medium are preferably located in one or more deflection regions of the housing 15.

Figure 6:
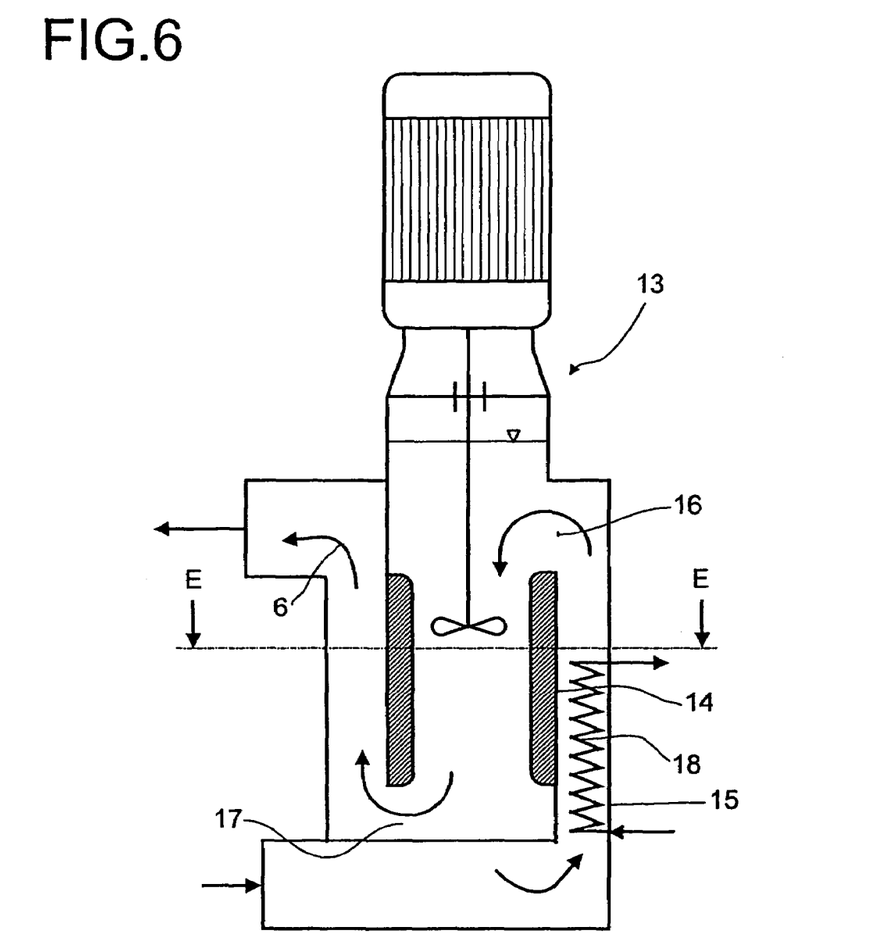
Figure 6A:
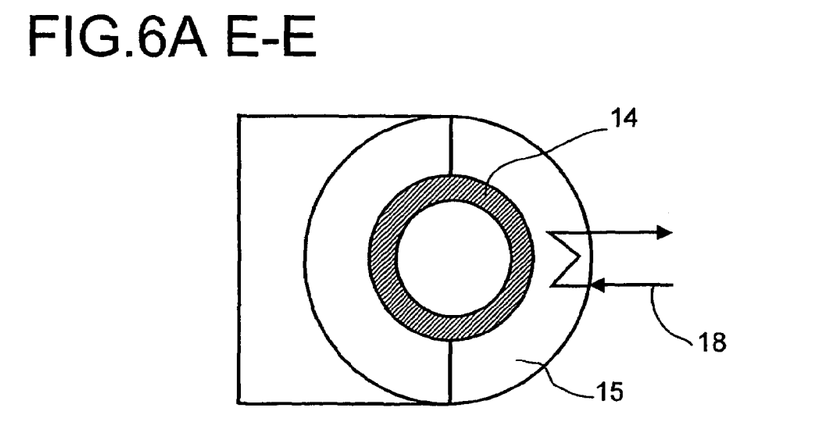

FIG. 6 shows a further variant of a pump 13 for deflection of the heat exchange medium 6 with cross section E-E in FIG. 6a, where, as a difference from the design shown in FIG. 5, the housing 15 is, as is clearly visible in the cross-sectional depiction in FIG. 6a, arranged with a circular cross section around the pump guide tube 14.

We claim:

1. A reactor for testing catalyst systems, comprising:
   a plurality of catalyst tubes arranged parallel to one another in an interior space of the reactor and whose ends are welded into tube plates, the plurality of catalyst tubes are grouped in two or more catalyst tube regions that are thermally separate from one another, and separation between individual catalyst tube regions is achieved by dummy tubes or solid round rods having a same external diameter as the catalyst tubes;
   caps at each end of the reactor which each bound a cap space, with a fluid reaction medium being fed by one cap space into the catalyst tubes, flowing through the catalyst tubes and being discharged by another cap space; and
   a heat exchange medium circuit in which a heat exchange medium is fed in at one end of the reactor, flows through an intermediate space between the catalyst tubes, and flows out at another end of the reactor.

2. A reactor for testing catalyst systems, comprising:
   a plurality of catalyst tubes arranged parallel to one another in an interior space of the reactor and whose ends are welded into tube plates, the plurality of catalyst tubes are grouped in two or more catalyst tube regions that are thermally separate from one another, and one or more of the catalyst tube regions are each provided with at least one catalyst tube having a sheath for accommodating a thermocouple and are otherwise filled with inert material, in particular a bed of $Al_2O_3$ and closed at least at one end;
   caps at each end of the reactor which each bound a cap space, with a fluid reaction medium being fed by one cap space into the catalyst tubes, flowing through the catalyst tubes and being discharged by another cap space; and
   a heat exchange medium circuit in which a heat exchange medium is fed in at one end of the reactor, flows through an intermediate space between the catalyst tubes, and flows out at another end of the reactor.

3. A reactor for testing catalyst systems, comprising:
   a plurality of catalyst tubes arranged parallel to one another in an interior space of the reactor and whose ends are welded into tube plates, the plurality of catalyst tubes are grouped in two or more catalyst tube regions that are thermally separate from one another, and one or more of the catalyst tube regions are each provided with one or more catalyst tubes with sheaths for accommodating sampling tubes and/or thermocouples;

caps at each end of the reactor which each bound a cap space, with a fluid reaction medium being fed by one cap space into the catalyst tubes, flowing through the catalyst tubes and being discharged by another cap space; and a heat exchange medium circuit in which a heat exchange medium is fed in at one end of the reactor, flows through an intermediate space between the catalyst tubes, and flows out at another end of the reactor.

4. A reactor for testing catalyst systems, comprising:

a plurality of catalyst tubes arranged parallel to one another in an interior space of the reactor and whose ends are welded into tube plates, the plurality of catalyst tubes are grouped in two or more catalyst tube regions that are thermally separate from one another, and the catalyst tubes in individual catalyst tube regions differ in at least one of their internal diameter and their spacing;

caps at each end of the reactor which each bound a cap space, with a fluid reaction medium being fed by one cap space into the catalyst tubes, flowing through the catalyst tubes and being discharged by another cap space; and a heat exchange medium circuit in which a heat exchange medium is fed in at one end of the reactor, flows through an intermediate space between the catalyst tubes, and flows out at another end of the reactor.

5. A reactor for testing catalyst systems, comprising:

a plurality of catalyst tubes arranged parallel to one another in an interior space of the reactor and whose ends are welded into tube plates, and the plurality of catalyst tubes are grouped in two or more catalyst tube regions that are thermally separate from one another;

caps at each end of the reactor which each bound a cap space, with a fluid reaction medium being fed by one cap space into the catalyst tubes, flowing through the catalyst tubes and being discharged by another cap space, and the cap space by which the reaction medium is taken off is divided by dividing walls so that the reaction medium can be taken off separately from each catalyst tube region; and a heat exchange medium circuit in which a heat exchange medium is fed in at one end of the reactor, flows through an intermediate space between the catalyst tubes, and flows out at another end of the reactor.

6. A reactor for testing catalyst systems, comprising:

a plurality of catalyst tubes arranged parallel to one another in an interior space of the reactor and whose ends are welded into tube plates, and the plurality of catalyst tubes are grouped in two or more catalyst tube regions that are thermally separate from one another;

caps at each end of the reactor which each bound a cap space, with a fluid reaction medium being fed by one cap space into the catalyst tubes, flowing through the catalyst tubes and being discharged by another cap space, and, in addition to or as an alternative to the cap space by which the reaction medium is taken off, the cap space by which the reaction medium is fed into is divided by dividing walls so that the reaction medium can be fed separately into the individual catalyst tube regions; and a heat exchange medium circuit in which a heat exchange medium is fed in at one end of the reactor, flows through an intermediate space between the catalyst tubes, and flows out at another end of the reactor.

7. A reactor for testing catalyst systems, comprising:

a plurality of catalyst tubes arranged parallel to one another in an interior space of the reactor and whose ends are welded into tube plates, and the plurality of catalyst tubes are grouped in two or more catalyst tube regions that are thermally separate from one another;

caps at each end of the reactor which each bound a cap space, with a fluid reaction medium being fed by one cap space into the catalyst tubes, flowing through the catalyst tubes and being discharged by another cap space; and a heat exchange medium circuit in which a heat exchange medium is introduced into an intermediate space between the catalyst tubes in an upper region of the reactor and discharged from a lower region of the reactor with the heat exchange medium taken off from the lower region of the reactor by a pump flowing into a housing that encloses the pump guide tube, flowing upward in the region between the interior wall of the housing and the outer wall of the pump guide tube, flowing into the interior space of the pump guide tube by an opening in the upper region of the pump guide tube, flowing from the top downward through this space, flowing into a further intermediate space between the interior wall of the housing and the outer wall of the pump guide by an opening in the lower region of the pump guide tube, flowing from the bottom upward through this intermediate space, and flowing into the upper region of the intermediate space between the catalyst tubes by an opening in the upper region of this space, wherein the reactor includes a vertical longitudinal axis.

8. A reactor as claimed in claim 7, wherein the housing has a rectangular cross section.

9. A reactor as claimed in claim 7, wherein the housing has a circular cross section.

* * * * *